(12) United States Patent
Hashimoto et al.

(10) Patent No.: US 8,737,710 B2
(45) Date of Patent: May 27, 2014

(54) ULTRASONIC DIAGNOSTIC APPARATUS, IMAGE PROCESSING APPARATUS AND IMAGE PROCESSING METHOD

(75) Inventors: Shinichi Hashimoto, Otawara (JP); Hiroyuki Ohuchi, Otawara (JP); Yasuhiko Abe, Otawara (JP); Masahide Nishiura, Machida (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 946 days.

(21) Appl. No.: 12/793,112

(22) Filed: Jun. 3, 2010

(65) Prior Publication Data

US 2010/0310145 A1 Dec. 9, 2010

(30) Foreign Application Priority Data

Jun. 3, 2009 (JP) ................................ 2009-134310

(51) Int. Cl.
| | | |
|---|---|---|
| *G06K 9/00* | (2006.01) | |
| *A61B 8/00* | (2006.01) | |
| *A61B 8/12* | (2006.01) | |
| *A61B 8/14* | (2006.01) | |

(52) U.S. Cl.
USPC .......................................... 382/131; 382/128

(58) Field of Classification Search
USPC ................... 382/128–132; 600/437, 443, 462
See application file for complete search history.

(56) References Cited

U.S. PATENT DOCUMENTS

| 2005/0256402 A1* | 11/2005 | Kawashima et al. ......... 600/437 |
| 2007/0036414 A1 | 2/2007 | Georgescu et al. |
| 2008/0051652 A1* | 2/2008 | Ichioka et al. ................ 600/437 |
| 2008/0077013 A1* | 3/2008 | Kawagishi et al. ........... 600/443 |

FOREIGN PATENT DOCUMENTS

| CN | 101152096 A | 4/2008 |
| JP | 2002-140689 A | 5/2002 |
| JP | 2007-319467 A | 12/2007 |
| JP | 2008-79805 A | 4/2008 |
| JP | 2009-72593 A | 4/2009 |
| WO | WO 2004/028375 A1 | 4/2004 |

OTHER PUBLICATIONS

Xiaoguang Lu, et al. "Autompr: Automatic Detection of Standard Planes in 3D Echocardiography," Siemens Corporate Research and Siemens Medical Solutions. IEEE, 2008. pp. 1279-1281.
Office Action issued Feb. 29, 2012 in Chinese Application No. 201010196474.X (With English Translation).
Office Action issued Aug. 20, 2013, in Japanese Patent Application No. 2009-134310 with English translation.

* cited by examiner

*Primary Examiner* — Joy Chng
(74) *Attorney, Agent, or Firm* — Oblon, Spivak, McClelland, Maier & Neustadt, L.L.P.

(57) ABSTRACT

According to one embodiment, an ultrasonic diagnostic apparatus comprises an ultrasonic probe, a scanning unit, an image data generating unit, a slice specifying unit, an image generating unit and a display unit. The scanning unit repeats three-dimensional scanning on a three-dimensional region in an object with an ultrasonic wave via the ultrasonic probe. The image data generating unit repeatedly generates three-dimensional image data based on an output from the scanning unit. The slice specifying unit specifies at least one slice from the three-dimensional image data concurrently with the three-dimensional scanning. The image generating unit generates at least one slice image associated with the specified slice from the three-dimensional image data. The display unit displays the generated slice image.

31 Claims, 6 Drawing Sheets

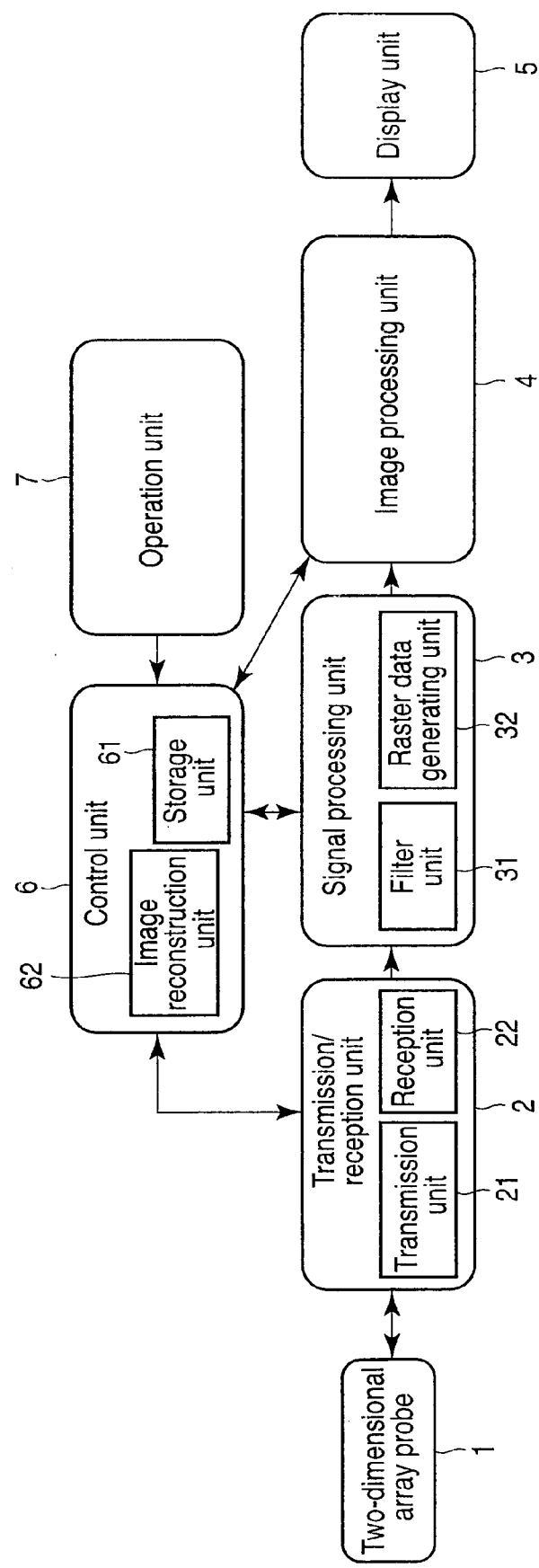
F I G. 1

4ch

2ch

3ch

SAX(apex)

SAX(mid)

SAX(base)

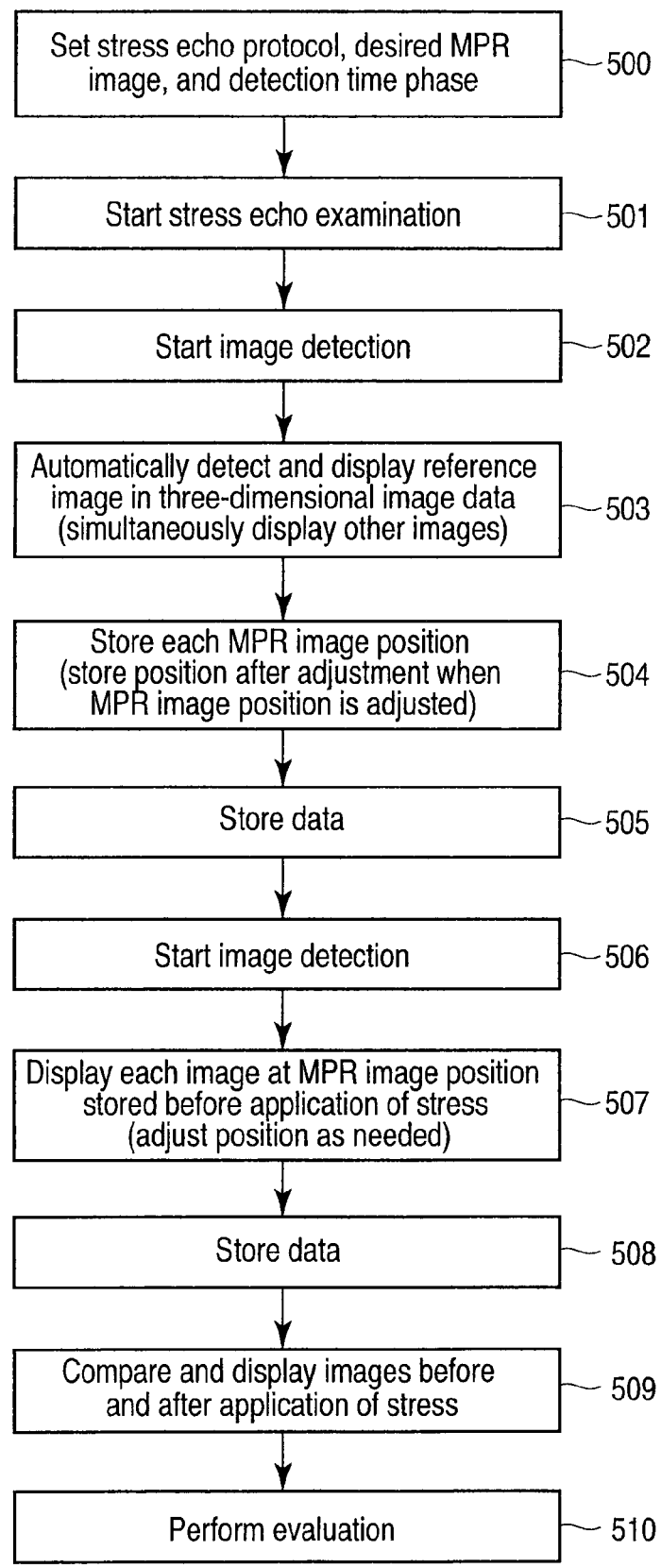
F I G. 5

Score display       MPR image
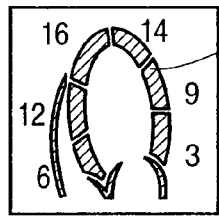 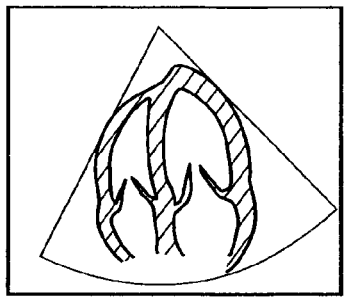
FIG. 6A      FIG. 6E     Four-chamber view
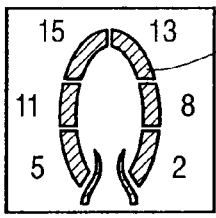 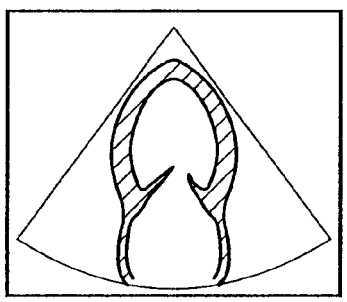
FIG. 6B      FIG. 6F     Two-chamber view
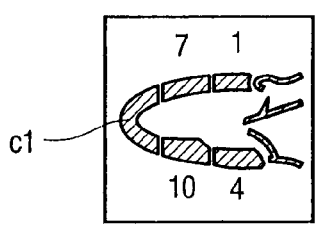 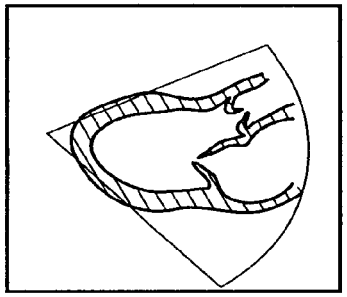
FIG. 6C      FIG. 6G     Three-chamber view
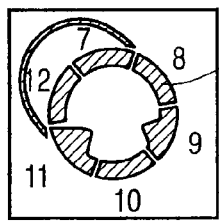 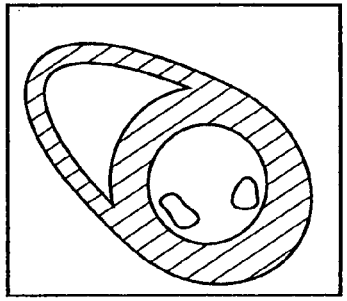
FIG. 6D      FIG. 6H     SAX

ULTRASONIC DIAGNOSTIC APPARATUS, IMAGE PROCESSING APPARATUS AND IMAGE PROCESSING METHOD

CROSS-REFERENCE TO RELATED APPLICATIONS

This application is based upon and claims the benefit of priority from Japanese Patent Application No. 2009-134310, filed Jun. 3, 2009; the entire contents of which are incorporated herein by reference.

FIELD

Embodiments described herein relate generally to an ultrasonic diagnostic apparatus, an image processing apparatus and an image processing method.

BACKGROUND

There is known an ultrasonic diagnostic apparatus which three-dimensionally scans an ultrasonic wave applied to an object and displays a three-dimensional image in real time. The ultrasonic diagnostic apparatus acquires three-dimensional ultrasonic images of an object by three-dimensionally scanning an ultrasonic beam and images the object. This apparatus can also reconstruct a slice image from an arbitrary imaging region (view) of a target anatomical region based on acquired three-dimensional image data by arithmetic processing.

The ultrasonic diagnostic apparatus is used to non-invasively examine an anatomical region in an object. The ultrasonic diagnostic apparatus can be suitably used for stress echo examination for cardiac function examination, in particular. In stress echo examination, first of all, this apparatus acquires ultrasonic images of a plurality of views of the heart under a predetermined protocol in a normal state of an object, i.e., a state before the application of stress (which will be referred to as a rest phase hereinafter). The apparatus then acquires ultrasonic images of a plurality of views of the heart again under the predetermined protocol in a state in which exercise stress or pharmacological stress is applied to the heart of the object to increase the heart rate, i.e., a state in which stress is applied to the heart (which will be referred to as a post phase hereinafter). Comparatively observing the images acquired in the different phases allows to evaluate the presence/absence of an ischemic region and a deterioration in cardiac function.

Stress echo examination, however, requires images from a plurality of views for the observation of the heart, and needs to quickly acquire data. In addition, since stress is applied to the heart of the object during examination, quick examination is required to minimize the load on the object.

According to existing techniques, first of all, an examiner (operator) acquires images of a plurality of views in a rest phase. The examiner then produces a state of a post phase by applying stress on the heart of the object, and acquires, in the post phase, images of the same views as those in the rest phase.

In such a procedure, however, the apparatus needs to acquire images of the same views as those in a rest phase before the heart rate decreases, with the heart rate being kept high. It is therefore not easy for the examiner to expertly display desired views. Such operation demands skill. That is, an unskilled examiner takes time and effort to perform such examination, resulting in a deterioration in operating efficiency. This leads to a great decrease in the number of examinations that can be performed per day.

BRIEF DESCRIPTION OF THE DRAWINGS

FIG. 1 is a functional block diagram showing a three-dimensional ultrasonic diagnostic apparatus according to the first embodiment;

FIG. 5 is a flowchart for explaining the operation of the fourth embodiment; and FIGS. 6A, 6B, 6C, 6D, 6E, 6F, 6G, and 6H are views for explaining the fifth embodiment.

DETAILED DESCRIPTION

Figure 2:
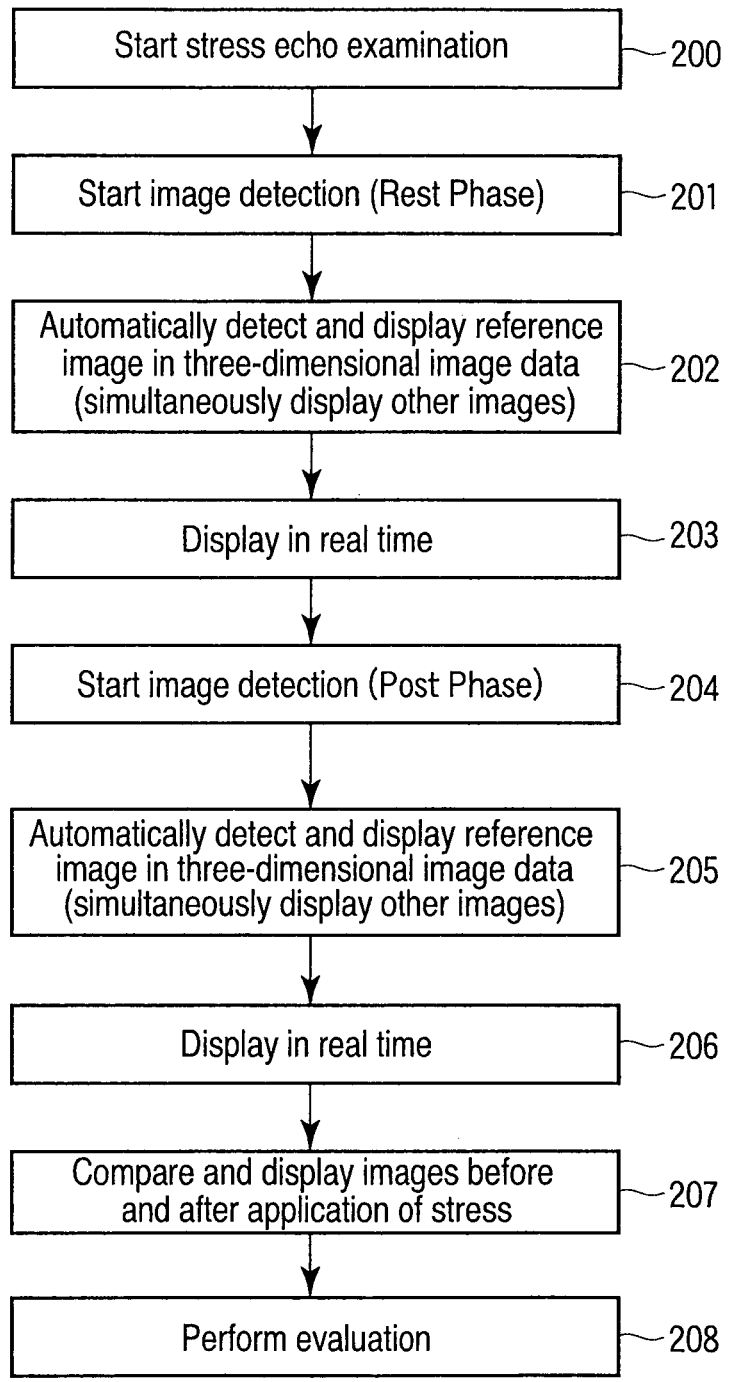
FIG. 2 is a flowchart for explaining the operation of the first embodiment.

In general, according to one embodiment, a plurality of embodiments will be described below. Stress echo examination on the heart, which is an example of an anatomical region in an object, will be described below.

(First Embodiment)

FIG. 1 is a functional block diagram showing a three-dimensional ultrasonic diagnostic apparatus according to the first embodiment. Referring to FIG. 1, reference numeral 1 denotes a two-dimensional array probe. The two-dimensional array probe 1 includes ultrasonic transducers arranged in a matrix form. The two-dimensional array probe 1 three-dimensionally scans and transmits an ultrasonic wave, and receives three-dimensional data as an echo signal.

The two-dimensional array probe 1 is connected to a transmission/reception unit 2. The transmission/reception unit 2 includes a transmission unit 21 and a reception unit 22. The transmission unit 21 supplies an electrical signal to the two-dimensional array probe 1 to make it generate an ultrasonic wave. The reception unit 22 receives an echo signal from the two-dimensional array probe 1. That is, the transmission/reception unit 2 repeatedly scans a three-dimensional region including a region of interest of an anatomical region in an object with an ultrasonic wave via the two-dimensional array probe 1.

The transmission unit 21 includes, for example, a clock generating circuit, transmission delay circuit, and pulser circuit (none of which are shown). The clock generating circuit decides the transmission timing of an ultrasonic signal and a transmission frequency. The transmission delay circuit executes transmission focus by delaying ultrasonic waves to be transmitted. The pulser circuit incorporates pulsers equal in number to individual channels corresponding to the respective ultrasonic transducers. The pulser circuit generates driving pulses at delayed transmission timings. The driving pulses are supplied to the respective ultrasonic transducers of the two-dimensional array probe 1.

The reception unit 22 includes a preamplifier circuit, A/D conversion circuit, and reception delay/addition circuit. The preamplifier circuit amplifies an echo signal output from each ultrasonic transducer of the two-dimensional array probe 1 for each reception channel. The A/D conversion circuit A/D-converts each amplified echo signal. The reception delay/addition circuit gives the A/D-converted echo signals delay times required to decide reception directivity and adds the delayed echo signals.

The transmission/reception unit 2 is connected to a signal processing unit 3. The signal processing unit 3 visualizes the amplitude information of an echo to generate B-mode ultrasonic raster data from the echo signal. The signal processing unit 3 includes a filter unit 31 and a raster data generating unit 32. The filter unit 31 performs bandpass filter processing for a signal transmitted from the transmission/reception unit 2. The raster data generating unit 32 generates B-mode ultrasonic raster data based on a signal output from the filter unit 31.

The signal processing unit 3 is connected to an image processing unit 4. The image processing unit 4 generates voxel data based on data after signal processing (B-mode ultrasonic raster data) which is output from the signal processing unit 3. The image processing unit 4 generates three-dimensional image data by performing volume rendering for this voxel data. The image processing unit 4 reconstructs an MPR (Multi Plane Reconstruction) image of an arbitrary slice of the object from the three-dimensional image data.

That is, the signal processing unit 3 and the image processing unit 4 repeatedly generate three-dimensional image data based on an output (B-mode ultrasonic raster data) from the signal processing unit 3 for each scanning period in which the transmission/reception unit 2 repeatedly three-dimensionally scans an ultrasonic wave.

The image processing unit 4 is connected to a display unit 5. The display unit 5 is, for example, a CRT (Cathode Ray Tube) or liquid crystal display, and displays three-dimensional image data, MPR image, or the like output from the image processing unit 4.

That is, the two-dimensional array probe 1, the transmission/reception unit 2, the signal processing unit 3, and the image processing unit 4 generate three-dimensional image data associated with the heart in the object. In stress echo examination, this embodiment generates three-dimensional image data in both a rest phase and a post phase.

Referring to FIG. 1, reference numeral 6 denotes a control unit. The control unit 6 includes a storage unit 61 and an image reconstruction unit 62. The storage unit 61 is a storage device such as a ROM (Read Only Memory) or RAM (Random Access Memory). The storage unit 61 stores various kinds of control programs and the like. The CPU (not shown) incorporated in the control unit 6 controls the transmission/reception unit 2, the signal processing unit 3, the image processing unit 4, and the like by processing the instructions written in control programs. The storage unit 61 stores the image data acquired in different phases in stress echo examination. The storage unit 61 further stores, as a reference image (sample image), an image, of the images (MPR images) of the views acquired in stress echo examination, which corresponds to a reference view. The first embodiment uses an image pattern of a four-chamber view, which is a four-chamber view image, as a reference.

The image reconstruction unit 62 reconstructs a slice image (MPR image) associated with a slice crossing a cardiac region from three-dimensional image data for each scanning period in which the transmission/reception unit 2 repeatedly three-dimensionally scans an ultrasonic wave. The image reconstruction unit 62 also reconstructs a slice image (MPR image) associated with a slice crossing a cardiac region from three-dimensional image data for each cardiac cycle. A cardiac cycle can be obtained by an ECG (Electro Cardio Gram).

The image reconstruction unit 62 reconstructs an MPR image of a slice set in, for example, an examination protocol from three-dimensional image data for each scanning period or each cardiac cycle. The image reconstruction unit 62 also reconstructs an MPR image of another slice from the reconstructed MPR image or simultaneously reconstructs a plurality of MPR images. This function will be described in detail later.

The control unit 6 is connected to an operation unit 7. The operation unit 7 is used to input various kinds of setting information. Pieces of information or instructions input by the operation unit 7 are supplied to the control unit 6. The control unit 6 executes processing based on these pieces of input information or instructions.

The control unit 6 controls the two-dimensional array probe 1, the transmission/reception unit 2, the signal processing unit 3, the image processing unit 4, and the image reconstruction unit 62 in a rest phase and a post phase each in a stress echo work flow. In this embodiment, the control unit 6 specifies a plurality of slice images crossing the cardiac region. When specifying a specific slice of the heart from three-dimensional image data in a rest phase, the control unit 6 repeats, in a post phase afterward, three-dimensional scanning of ultrasonic waves, generation of three-dimensional image data, and generation of three-dimensional image data of a slice image associated with the slice specified in the rest phase.

Alternatively, when specifying a slice image as a reference from three-dimensional image data in a rest phase, the control unit 6 repeats, in a post phase afterward, three-dimensional scanning of ultrasonic waves, generation of three-dimensional image data, generation of a plurality of slice images from the three-dimensional image data, and selection of an image from the plurality of slice images based on the slice image specified in the rest phase.

FIG. 2 is a flowchart showing an example of a stress echo work flow. Referring to FIG. 2, when starting stress echo examination in step 200, the control unit 6 starts detection processing for an image in a rest phase in step 201. In this step, the control unit 6 acquires an image without any stress on the heart of the object.

In step 201, the control unit 6 starts a procedure in a rest phase. In this step, the examiner brings the two-dimensional array probe 1 into contact with the object, and positions the two-dimensional array probe 1 to set the entire region of interest (the left ventricle) of the heart in the scanning area. With the operation of the examiner, the transmission unit 21 of the transmission/reception unit 2 supplies an electrical signal to the two-dimensional array probe 1 to generate an ultrasonic wave and apply it to the object. The two-dimensional array probe 1 captures an echo signal reflected by the object. The reception unit 22 receives the signal. The transmission/reception unit 2 supplies the obtained reception signal to the signal processing unit 3. The filter unit 31 then performs bandpass filter processing for the signal. The resultant output is supplied to the raster data generating unit 32. The raster data generating unit 32 generates B-mode ultrasonic raster data.

The image processing unit 4 generates a volume rendering image as a three-dimensional image or an MPR image based on the B-mode ultrasonic rater data output from the signal processing unit 3. In this manner, the control unit 6 acquires three-dimensional image data about the region of interest (the left ventricle) of the heart.

The control unit 6 acquires three-dimensional image data over one or more cardiac cycles of the heart. The image processing unit 4 reconstructs an MPR image of a necessary view from three-dimensional image data for each ultrasonic scanning period. The display unit 5 displays the reconstructed MPR image.

In step 202, the control unit 6 detects a reference MPR image, i.e., the slice image of a reference view, from the acquired three-dimensional image data. The first embodiment uses a four-chamber view image as a reference MPR image. This processing is also called automatic detection. An example of automatic detection processing will be described below.

The control unit 6 extracts a left ventricular wall annulus portion or mitral annulus portion, which is relatively easy to recognize, from a plurality of MPR images. The control unit 6 then positions a remote point remotest from the annulus portion in the left ventricular chamber, and sets a straight line connecting the remote point and the central portion of the mitral annulus as a left ventricular center axis.

The control unit 6 then rotates a view about this left ventricular center axis to generate a plurality of MPR images of different slices. The control unit 6 performs pattern matching processing by comparing the plurality of MPR images obtained in this process with the reference image (four-chamber view image) stored in the storage unit 61. The control unit 6 then extracts an MPR image most similar to the four-chamber view of the reference image as a reference image of the four-chamber view.

Figure 3A:
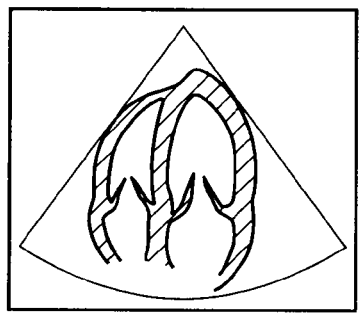
FIGS. 3A, 3B, 3C, 3D, 3E, and 3F are views each showing an example of an image of each of views detected in different phases according to the first embodiment.
Figure 3B:
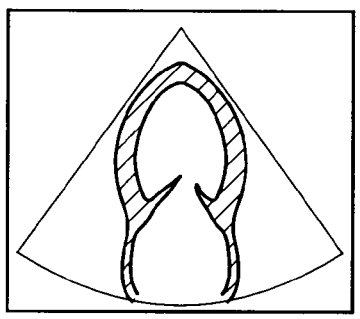
Figure 3C:
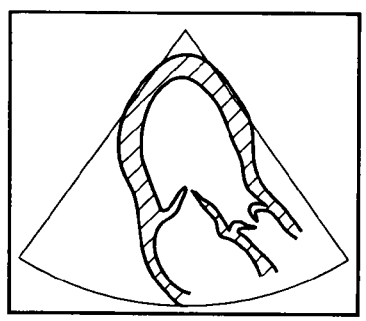
Figure 3D:
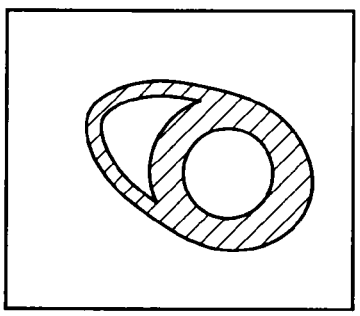
Figure 3E:
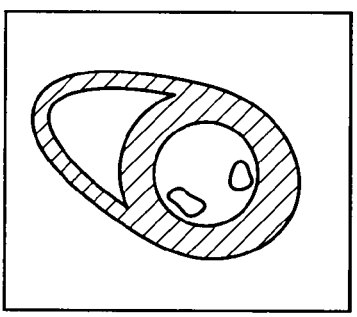

The control unit 6 then further rotates the MPR image about the left ventricular center axis with the extracted four-chamber view being a starting point to decide MPR images at 60° and 270° from the four-chamber view as a two-chamber view (two-chamber image) and a three-chamber view (three-chamber image), respectively. The control unit 6 further extracts a short-axis image (SAX) perpendicular to the left ventricular center axis by dividing the portion between a cardiac apex portion and an annulus portion into three equal parts. That is, the control unit 6 decides slices of Apical (apical portion), Mid (middle portion), and Base (base portion) as short-axis images located in the centers of the respective divided parts. FIGS. 3A, 3B, and 3C respectively show the images of the four-chamber view, two-chamber view, and three-chamber view obtained in this manner. FIGS. 3D, 3E, ad 3F show the slice images of Apical, Mid, and Base, respectively. Obviously, it is possible to search for each slice and display it separately.

A stress echo protocol sometimes uses views other than those shown in FIGS. 3A to 3C. However, since it is possible to extract other views in the same manner as described above, the first embodiment will exemplify the views shown in FIGS. 3A to 3C.

The control unit 6 repeatedly executes the automatic detection process for images in step 202 for each ultrasonic scanning interval. That is, the control unit 6 repeatedly executes the extraction of an MPR image as a reference and the extraction of MPR images of other views based on the reference image in real time for each scanning interval. The control unit 6 then displays each view image reconstructed in step 203 on the display unit 5 in real time.

The heart moves in cardiac cycles, and exhibits different shapes at the respective time phases in a cardiac cycle. For this reason, an MPR image may be extracted (detected) for each cardiac cycle. In this case, an MPR image is updated for each frame, but the MPR position is updated for each cardiac cycle. Note that which time phase in a cardiac cycle is selected will be described later.

In step 204, the control unit 6 starts detection processing for an image in a post phase. Note that the storage unit 61 stores the three-dimensional image data acquired in the rest phase, the reconstructed MPR image data, and the like before the process advances to step 204.

In step 204, the control unit 6 acquires images while the heartbeat of the object is raised by applying exercise or pharmacological stress on the heart. In step 204, as in step 201, the examiner brings the two-dimensional array probe 1 into contact with the object and positions the two-dimensional array probe 1 to set the entire region of interest (the left ventricle) of the heart in the scanning area. With the operation of the examiner, the two-dimensional array probe 1 generates an ultrasonic wave. The two-dimensional array probe 1 receives an echo from the object. The control unit 6 generates three-dimensional image data based on the received echo signal.

In step 205, the control unit 6 reconstructs a reference MPR image, i.e., a slice image of a reference view, from the acquired three-dimensional image data. In the first embodiment, the control unit 6 detects an image of a four-channel view. In step 205, as in step 202, the control unit 6 extracts, as a reference image, an MPR image most similar to the reference image (four-chamber view image) stored in the storage unit 61 by pattern matching with the reference image. The control unit 6 decides an MPR image at an angle of 60° from this reference image as a two-chamber view. The control unit 6 also decides an MPR image at an angle of 270° from this reference image as a three-chamber view. The control unit 6 further decides slices of Apical (apical portion), Mid (middle portion), and Base (base portion) as short-axis images (SAX) perpendicular to the left ventricular center axis.

Figure 3F:
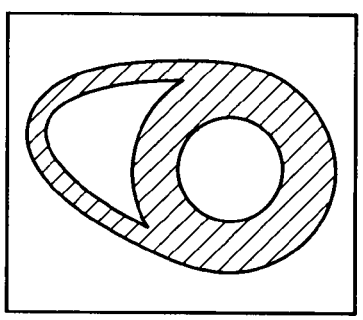

With the above process, the control unit 6 reconstructs four-chamber view images (four-, two-, and three-channel view images) like those shown in FIGS. 3A, 3B, and 3C and slice images of Apical, Mid, and Base like those shown in FIGS. 3D, 3E, and 3F. The control unit 6 displays the reconstructed images of the respective views on the display unit 5 in real time in step 206. The control unit 6 causes the storage unit 61 to store the three-dimensional image data acquired in the post phase, the reconstructed MPR image data, and the like.

In step 207, the control unit 6 displays the respective images in the rest and post phases stored in the storage unit 61 on the display unit 5 side by side. In step 208, the control unit 6 compares these images and evaluates the degrees of matching between them.

The first embodiment provides the ultrasonic diagnostic apparatus with the function of detecting a four-chamber view as a reference from MPR images obtained from three-dimensional image data. That is, this function extracts, as a reference fourth-chamber view image, an MPR image most similar to a reference image stored in advance by pattern matching. This apparatus is configured to automatically decide a two-chamber view image, a three-chamber view image, and the like as other necessary views in addition to four-chamber image data as a reference.

With this arrangement, according to the first embodiment, it is possible to automatically acquire not only a four-chamber view as a reference but also other view images such as a two-chamber view image and a three-chamber view image by one acquisition (one or more heartbeat) of three-dimensional image data.

An existing technique needs to perform image acquisition a plurality of number of times by, for example, acquiring a plurality of views in a rest phase by moving the probe position and acquiring identical views in a post phase. In addition, it is necessary to adjust the probe position for each image acquisition. In addition, when acquiring views in a post phase, it is necessary to adjust each slice to a corresponding view in the rest phase while seeing the image in the rest phase. This operation is complicated and difficult in terms of manipulation and operation.

In contrast to this, the first embodiment can greatly shorten the image acquisition time necessary for stress echo examination and dramatically improve the operating efficiency of stress echo examination. In addition, before image evaluation, the examiner (operator) needs only to concentrate his/her attention on setting of the image acquisition position of the probe. This can therefore lower the level of skill required for image acquisition.

In addition, the first embodiment reconstructs an MPR image of each view necessary for stress echo examination for each ultrasonic scanning interval and displays each reconstructed image on the display unit 5 in real time. This can further improve the convenience for the examiner.

Note that the first embodiment is configured to detect a four-chamber view as a reference by pattern matching. However, it is possible to decide a widest view in a heart chamber area as a four-chamber view.

(Second Embodiment)

The first embodiment has disclosed the case of detecting a four-chamber view image as a reference image. In order to extract each view image from three-dimensional image data in actual stress echo examination, a very important point is to extract which view image is used as a reference image. Accurately extracting a reference image makes it possible to relatively easily extract other view images based on the relative positional relationship between them and the reference image.

Calculating the characteristic shape of the heart from an overall image pattern including portions (the right ventricle and the left atrium or the left ventricle) in addition to the left ventricle can extract a desired view image more accurately. If, however, a four-chamber view or two-chamber view is set as a reference image, it is sometimes impossible to clearly recognize the surrounding shape of the heart. In such a case, it is difficult to specify a four-chamber (two-chamber) view image from only the left ventricular shape, resulting in a deterioration in extraction accuracy.

In contrast to this, a three-chamber view image, which is a three-chamber view of the left ventricle, is an image including the left ventricle and aorta, and the shape of the left ventricle itself is also characteristic. In addition, the spatial area from which a three-chamber view is obtained is limited. According to the second embodiment, therefore, a three-chamber view image is used as a reference image, and an image pattern of such a three-chamber view is stored as a reference image in a storage unit 61.

In the same procedure as that described in the first embodiment, three-chamber views as references are detected in rest and post phases. MPR images at angles of 60° and 270° from the detected three-chamber view as a reference point are respectively decided as a four-chamber view and a two-chamber view. In addition, slices of Apical (apical portion), Mid (middle portion), and Base (base portion) are decided as short-axis images (SAX) perpendicular to the three-chamber view.

Using a three-chamber view as a reference image in this manner can further improve the detection accuracy of other view images (two-chamber view and four-chamber view) from the characteristics of the three-chamber view.

(Third Embodiment)

The first and second embodiments prepare a reference image (MPR image) in advance and make the storage unit 61 store the image pattern as a reference image. There are many variations of the examination protocol for stress echo examination. The protocol includes many elements such as selection of the number of times of examination after the application of pharmacological stress and of an examination slice. Therefore, a detected MPR image is not always an MPR image desired by the examiner.

The third embodiment is therefore configured to allow to set an MPR image of a view (view image) desired by the examiner and a desired detection time phase (cardiac time phase) when performing protocol setting for stress echo examination. That is, this embodiment allows to detect a view and an MPR image at a time phase corresponding to the examination protocol set in the apparatus. That is, the embodiment makes a storage unit 61 store image data corresponding to the view and time phase set in the examination protocol as a reference image in advance.

Figure 4:
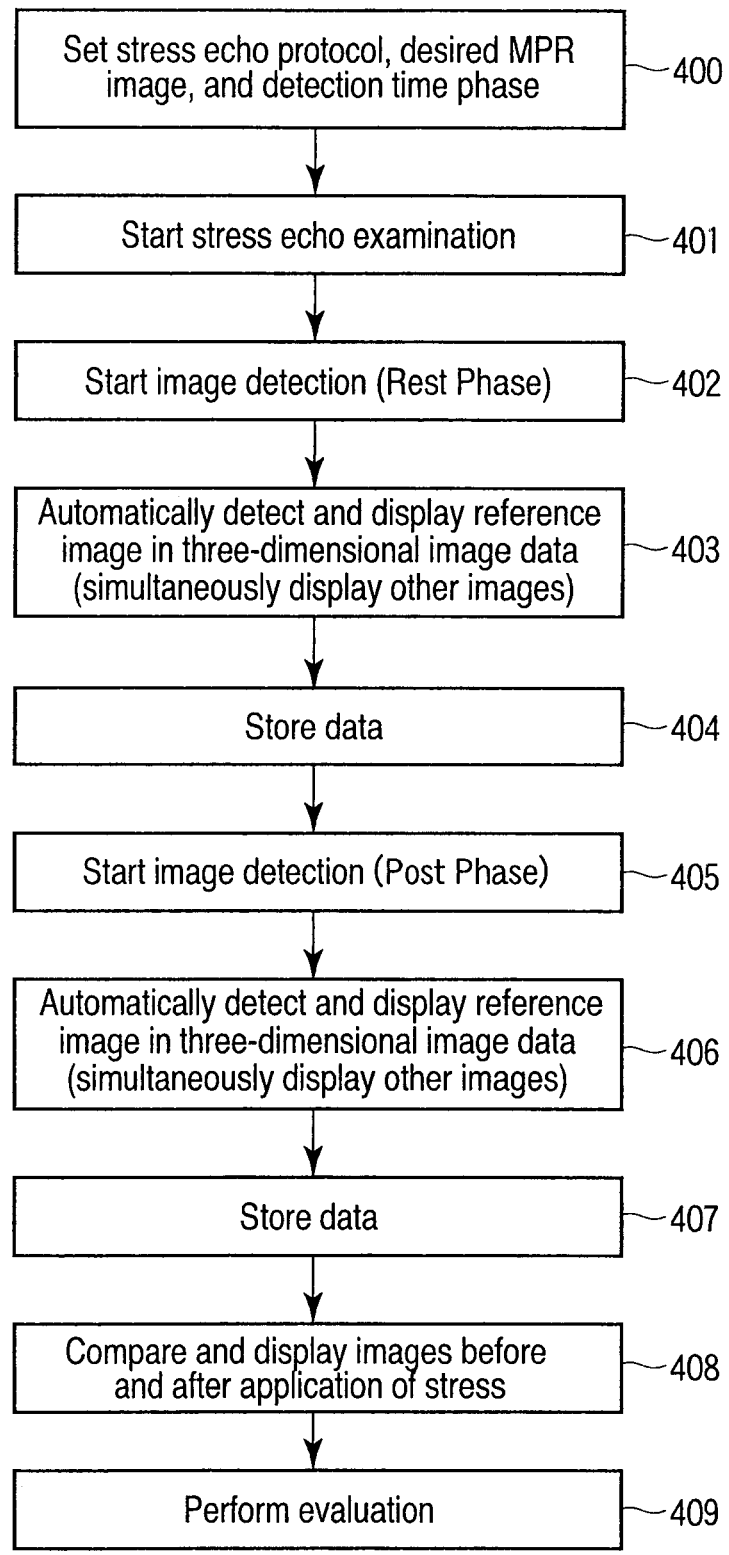
FIG. 4 is a flowchart for explaining the operation of the third embodiment.

As shown in FIG. 4, in the third embodiment, a stress echo protocol is set in step 400. In this step, the examiner sets a desired MPR image (view image) and a corresponding detection time phase (cardiac time phase) together with a protocol. From step 401, the process shifts to the processing for detecting images in a rest phase and the processing for detecting images in a post phase. The processing in steps 401 to 409 corresponds to the processing in steps 200 to 208 in the first embodiment described with reference to FIG. 2.

A control unit 6 detects the MPR images (or the cardiac time phases of the MPR images) set in the stress echo protocol from three-dimensional image data in a rest phase and a post phase. The control unit 6 detects other MPR images based on the detected MPR images. Alternatively, the control unit 6 may select and switch predetermined MPR images or cardiac time phases after the acquisition of data.

According to the third embodiment, in stress echo protocol setting, this apparatus is provided with a function of setting a desired MPR image (view image), and hence MPR images are detected in the order set in the protocol. A display unit 5 then displays the detected MPR images. This makes it possible to display desired MPR images from three-dimensional image data. It is therefore possible to sequentially display views necessary for stress echo examination.

When executing stress echo examination using a three-chamber view or four-chamber view, the examiner sets these views in the stress echo protocol in advance. With this operation, images of views desired by the examiner are automatically detected. According to the third embodiment, it is possible to greatly shorten the detection time for images of views necessary for stress echo examination and the examination time.

In addition, in stress protocol setting, setting time phases (cardiac time phases) at which MPR images are to be detected can quickly acquire MPR images at desired time phases. This can complete the processing in a shorter time than when detecting images at all the time phases. According to the third embodiment, setting optimal time phases for each examiner can further make improvements in terms of detection accuracy and detection time.

(Fourth Embodiment)

According to the first and second embodiments, in a post phase, the same operation as that performed in a rest phase to detect MPR images (view images) is performed. Since the position of the probe pressed against the object hardly changes in the respective phases in many cases, the position of an MPR image relative to three-dimensional image data does not greatly change in many cases.

For this reason, the fourth embodiment is provided with a function of storing the positional information of MPR images relative to three-dimensional image data, which are extracted in a rest phase, in advance and detecting MPR images corresponding to the positional information of the MPR images in the rest phase in initial display operation in a post phase.

As shown in FIG. 5, in step 500, the examiner sets a stress echo protocol by using a protocol editor and the like. The examiner sets both desired MPR images (view images) and corresponding detection time phases (cardiac time phases) in addition to protocol setting. The process then advances to the image detection procedure in a rest phase (step 501 and subsequent steps). The operation in steps 501 to 503 corresponds to the operation in steps 200 to 202 in the first embodiment described with reference to FIG. 2.

In steps 501 to 503, a control unit 6 detects a predetermined MPR image (or the cardiac time phase of an MPR image) set from three-dimensional image data in advance by the stress echo protocol in a rest phase. The control unit 6 also detects other necessary MPR images based on this detected MPR image.

When the process advances to step 504, a storage unit 61 stores the positional information of each MPR image relative to three-dimensional image data which has been detected in the rest phase. In this case, the position of an MPR image may be finely adjusted by the processing performed by the control unit 6 or scanning performed by the examiner. In such a case, the control unit 6 causes the storage unit 61 to store the position of the MPR image after the adjustment. In step 505, the control unit 6 causes the storage unit 61 to also store the data of the detected three-dimensional image data.

The process then advances to step 506 to start detecting MPR images in a post phase. The control unit 6 performs MPR image detection in the post phase based on the positional information of the MPR images in the rest phase stored in step 504. In step 507, the control unit 6 displays the MPR images detected based on the positional information as MPR images in the post phase. If the position of the MPR images in the rest phase have been adjusted, the control unit 6 displays the MPR images after the positional adjustment.

In step 508, the control unit 6 causes the storage unit 61 to store these image data. In step 509, the control unit 6 causes a display unit 5 to display the images in the rest phase and the images in the post phase, which are stored in the storage unit 61, side by side. In step 510, the examiner evaluates the cardiac function by comparing the images in the rest and post phases.

The fourth embodiment is configured to store, in advance, the positional information of MPR images detected in a rest phase and use the positional information of the MPR images in the rest phase for MPR image detection in post phase. This can shorten the detection time and improve the detection accuracy. This can also make MPR images (view images) in different phases become more similar to each other. Even if an offset has occurred between initial display slices, providing the embodiment with a function of finely adjusting the offset or performing detection again can display corrected MPR images.

There is also available a technique of further improving the accuracy of the positions of MPR images. That is, the examiner manually detects an MPR image in a rest phase and stores its position in the storage unit 61. In a post phase, the control unit 6 detects an MPR image based on the positional information in the rest phase. This can detect a desired MPR image with higher accuracy.

(Modification of Fourth Embodiment)

It is conceivable to use the following procedure instead of the above procedure. For example, the control unit 6 causes the storage unit 61 to store the image pattern of an MPR image detected in rest phase. In a post phase, the control unit 6 detects an MPR image by referring to the stored image pattern. This makes it possible to extract the MPR images of identical views before and after the application of stress on the heart within a short period of time.

(Fifth Embodiment)

FIGS. 6A, 6B, 6C, 6D, 6E, 6F, 6G, and 6H are views for explaining the fifth embodiment. FIGS. 6A, 6B, 6C, and 6D each are an example of a schematic view used to express the systolic/diastolic function of the heart. Each schematic view displays the indexes obtained by segmenting a region of interest of the heart into a plurality of regions (segments) and grading the function of the cardiac wall for each segment. Such a schematic view is often used to evaluate the cardiac function by stress echo examination. There are various kinds of techniques available to segment a region of interest into a plurality of segments. For example, the technique recommended by ASE (American Society of Echocardiography) can be used.

It is possible to detect an MPR image of an arbitrary view from three-dimensional image data. Consider, for example, MPR images of a four-chamber view, two-chamber view, three-chamber view, and SAX view. The images of the four-chamber view, two-chamber view, and three-chamber view obtained by a protocol based on scanning from a cardiac apex portion of the heart are almost the same as the images obtained by two-dimensional scanning. However, an image of a SAX view obtained by scanning from the cardiac apex portion is an image from a probe position different from that in normal two-dimensional scanning operation. Therefore, without any processing, the SAX image is displayed in a direction different from that in a normally used schematic view.

The fifth embodiment is, therefore, provided with a means for changing the display directions of MPR images detected in different phases to the same directions as those in schematic views with a score notation used for stress echo examination. More specifically, the control unit 6 changes the views of the MPR images in FIGS. 6E, 6F, 6G, and 6H, which are MPR images of a four-chamber view, two-chamber view, three-chamber view, and SAX view, in accordance with the schematic views of FIGS. 6A, 6B, 6C, and 6D. FIG. 6A corresponds to the schematic view of the four-chamber view. FIG. 6B corresponds to the schematic view of the two-chamber view. FIG. 6C corresponds to the schematic view of the three-chamber view. FIG. 6D corresponds to the schematic view of the SAX view.

In the fifth embodiment, the control unit 6 displays marks representing slices associated with the MPR images of the four-chamber view, two-chamber view, three-chamber view, and SAX view in accordance with the directions of the schematic views with the score notation of the respective slice images.

According to the fifth embodiment, it is possible to display the MPR images of the four-chamber view, two-chamber view, three-chamber view, and SAX view with their display directions matching the display directions in schematic views with a score notation. This allows the examiner to understand the contents of an examination result more easily when evaluating the result, and hence can implement accurate stress echo examination. In addition, superimposing and displaying segments a1 to d1 constituting the score notation (FIGS. 6A, 6B, 6C, and 6D) on the respective MPR images (FIGS. 6E, 6F, 6G, and 6H) can further facilitate the comprehension of image positions for comparison.

According to each embodiment described above, it is possible to quickly and easily detect MPR images necessary for observation in stress echo examination for each phase. This can therefore shorten the detection time for MPR images and improve the examination efficiency.

In addition, according to each embodiment described above, it is possible to quickly detect an optimal MPR image necessary for stress echo examination by setting an MPR image or cardiac time phase in a protocol setting function for stress echo examination.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
   an ultrasonic probe;
   a scanning unit configured to repeat three-dimensional scanning on a three-dimensional region in an object with an ultrasonic wave via the ultrasonic probe;
   an image data generating unit configured to repeatedly generate three-dimensional image data based on an output from the scanning unit;
   a slice specifying unit configured to specify a slice from the three-dimensional image data concurrently with the three-dimensional scanning, wherein the slice specifying unit is configured to perform pattern matching between a sample image and MPR images obtained by rotating a slice angle around a calculated center axis to obtain a reference MPR image;
   an image generating unit configured to generate at least one slice image associated with the specified slice from the three-dimensional image data; and
   a display configured to display the generated slice image.

2. The apparatus according to claim 1, wherein the slice specifying unit specifies a plurality of slices crossing a cardiac region.

3. The apparatus according to claim 1, wherein the slice specifying unit specifies a slice corresponding to a three-chamber portion of a left ventricle of the heart.

4. The apparatus according to claim 1, wherein the image generating unit generates a slice image at a time phase set in a protocol for stress echo examination.

5. The apparatus according to claim 1, wherein the slice specifying unit specifies the slice from three-dimensional image data generated in a rest phase before application of stress in stress echo examination, and
   the image generating unit generates a slice image associated with the slice specified in the rest phase, from three-dimensional image data generated in a post phase after application of stress in the stress echo examination.

6. The apparatus according to claim 5, wherein the slice specifying unit specifies the slice from three-dimensional image data generated at a specific cardiac time phase in the rest phase.

7. The apparatus according to claim 1, wherein the slice specifying unit selects a slice image exhibiting a highest correlation coefficient relative to a reference slice image provided in advance, from a plurality of slice images generated from three-dimensional image data generated in a rest phase before application of stress in stress echo examination, and
   the image generating unit generates a slice image associated with a slice corresponding to the slice image selected in the rest phase, from three-dimensional image data generated in a post phase after application of stress in the stress echo examination.

8. The apparatus according to claim 7, wherein the slice specifying unit selects the slice image from a plurality of slice images generated from three-dimensional image data generated at a specific cardiac time phase in the rest phase.

9. The apparatus according to claim 1, wherein the slice specifying unit selects, as a second reference slice image, a slice image approximate to a first reference slice image provided in advance from a plurality of slice images generated from three-dimensional image data generated in a rest phase before application of stress in stress echo examination, and
   the image generating unit generates a plurality of slice images associated with a slice corresponding to the second reference slice image selected in the rest phase, from three-dimensional image data generated in a post phase after application of stress in the stress echo examination, and selects a slice image approximate to the second reference slice image from the plurality of slice images.

10. The apparatus according to claim 9, wherein the slice specifying unit selects the second slice image from a plurality of slice images generated from three-dimensional image data generated at a specific cardiac time phase in the rest phase.

11. The apparatus according to claim 1, wherein in accordance with a direction of a schematic view of the slice image with a score notation, the display displays a mark representing a slice associated with a slice image generated by the image generating unit.

12. An ultrasonic diagnostic apparatus, comprising:
    an ultrasonic probe;
    a scanning unit configured to scan a three-dimensional region in an object with an ultrasonic wave via the ultrasonic probe;
    an image data generating unit configured to generate three-dimensional image data based on an output from the scanning unit;
    a slice specifying unit configured to specify a slice from the three-dimensional image data, wherein the slice specifying unit is configured to perform pattern matching between a sample image and MPR images obtained by rotating a slice angle around a calculated center axis to obtain a reference MPR image;
    an image generating unit configured to generate a slice image associated with the specified slice, from the three-dimensional image data;
    a display configured to display the generated slice image; and
    a control unit configured to control the scanning unit, the image data generating unit, the slice specifying unit, the image generating unit, and the display so as to specify the slice from the three-dimensional image data in a first phase, repeatedly generate the three-dimensional image data by repeating the three-dimensional scanning in a second phase after the first phase, and generate and display a slice image associated with a slice specified in the first phase, from the three-dimensional image data.

13. The apparatus according to claim 12, wherein the slice specifying unit specifies a plurality of slices crossing a cardiac region, and
    the control unit controls the image generating unit to generate a plurality of slice images of different imaging regions.

14. The apparatus according to claim 12, wherein the slice specifying unit specifies a slice corresponding to a three-chamber portion of a left ventricle of the heart.

15. The apparatus according to claim 12, wherein the control unit controls the image generating unit to generate a slice image at a time phase set in a protocol for stress echo examination.

16. The apparatus according to claim 12, wherein the slice specifying unit selects a slice image exhibiting a highest correlation coefficient relative to a reference slice image provided in advance, from a plurality of slice images generated from three-dimensional image data generated in a rest phase before application of stress in stress echo examination, and the image generating unit generates a slice image associated with a slice corresponding to the slice image selected in a rest phase, from three-dimensional image data generated in a post phase after application of stress in the stress echo examination.

17. The apparatus according to claim 16, wherein the slice specifying unit selects the slice image from a plurality of slice images generated from three-dimensional image data generated at a specific cardiac time phase in the rest phase.

18. The apparatus according to claim 12, wherein the control unit controls the display to display, in accordance with a direction of a schematic view of the slice image with a score notation, a mark representing a slice associated with a slice image generated by the image generating unit.

19. An ultrasonic diagnostic apparatus, comprising:
an ultrasonic probe;
a scanning unit configured to scan a three-dimensional region in an object with an ultrasonic wave via the ultrasonic probe;
an image data generating unit configured to generate three-dimensional image data based on an output from the scanning unit;
an image generating unit configured to generate a slice image from the three-dimensional image data;
a display configured to display the generated slice image; and
a control unit configured to control the scanning unit, the image data generating unit, the image generating unit, and the display so as to select a reference slice image from a plurality of slice images generated from the three-dimensional image data in a first phase, repeatedly generate the three-dimensional image data by repeating the three-dimensional scanning in a second phase after the first phase, and select and display, using pattern matching, a slice image exhibiting a highest correlation coefficient relative to the reference slice image selected in the first phase from a plurality of slice images generated from the three-dimensional image data by rotating a slice angle around a calculated center axis.

20. The apparatus according to claim 19, wherein the reference slice image is selected from the plurality of slice images, which are generated from three-dimensional image data generated at a specific cardiac time phase in the first phase.

21. The apparatus according to claim 20, wherein the slice image is selected from the plurality of slice images, which are generated from three-dimensional image data generated at the specific cardiac time phase in the second phase.

22. The apparatus according to claim 19, wherein the plurality of slice images correspond to a plurality of predetermined slices crossing a cardiac region.

23. The apparatus according to claim 19, wherein the plurality of slices are slices in which anyone of a four-chamber portion, a three-chamber portion, and a two-chamber portion of a heart exists.

24. An image processing apparatus used for an ultrasonic diagnostic apparatus comprising an ultrasonic probe and a scanning unit configured to repeat three-dimensional scanning on a three-dimensional region in an object with an ultrasonic wave via the ultrasonic probe, the apparatus comprising:

an image data generating unit configured to repeatedly generate three-dimensional image data based on an output from the scanning unit;
a slice specifying unit configured to specify a slice from the three-dimensional image data concurrently with the three-dimensional scanning, wherein the slice specifying unit is configured to perform pattern matching between a sample image and MPR images obtained by rotating a slice angle around a calculated center axis to obtain a reference MPR image;
an image generating unit configured to generate a slice image associated with the specified slice from the three-dimensional image data; and
a display configured to display the generated slice image.

25. An image processing apparatus used for an ultrasonic diagnostic apparatus comprising an ultrasonic probe and a scanning unit configured to scan a three-dimensional region in an object with an ultrasonic wave via the ultrasonic probe, the apparatus comprising:

an image data generating unit configured to generate three-dimensional image data based on an output from the scanning unit;
a slice specifying unit configured to specify a slice from the three-dimensional image data, wherein the slice specifying unit is configured to perform pattern matching between a sample image and MPR images obtained by rotating a slice angle around a calculated center axis to obtain a reference MPR image;
an image generating unit configured to generate a slice image associated with the specified slice, from the three-dimensional image data;
a display configured to display the generated slice image; and
a control unit configured to control the scanning unit, the image data generating unit, the slice specifying unit, the image generating unit, and the display so as to specify the slice from the three-dimensional image data in a first phase, repeatedly generate the three-dimensional image data by repeating the three-dimensional scanning in a second phase after the first phase, and generate and display a slice image associated with a slice specified in the first phase, from the three-dimensional image data.

26. An image processing apparatus used for an ultrasonic diagnostic apparatus comprising an ultrasonic probe and a scanning unit configured to scan a three-dimensional region in an object with an ultrasonic wave via the ultrasonic probe, the apparatus comprising:

an image data generating unit configured to generate three-dimensional image data based on an output from the scanning unit;
an image generating unit configured to generate a slice image from the three-dimensional image data;
a display configured to display the generated slice image; and
a control unit configured to control the scanning unit, the image data generating unit, the image generating unit, and the display so as to select a reference slice image from a plurality of slice images generated from the three-dimensional image data in a first phase, repeatedly generate the three-dimensional image data by repeating the three-dimensional scanning in a second phase after the first phase, and select and display, using pattern matching, a slice image exhibiting a highest correlation coefficient relative to the reference slice image selected in the first phase, from a plurality of slice images generated from the three-dimensional image data by rotating a slice angle around a calculated center axis.

27. An image processing method used in an ultrasonic diagnostic apparatus comprising an ultrasonic probe and a scanning unit configured to scan a three-dimensional region in an object with an ultrasonic wave via the ultrasonic probe, the method comprising:

repeatedly generating three-dimensional image data based on an output from the scanning unit;

specifying a slice from the three-dimensional image data concurrently with the three-dimensional scanning, the specifying step including performing pattern matching between a sample image and MPR images obtained by rotating a slice angle around a calculated center axis to obtain a reference MPR image;

generating at least one slice image associated with the specified slice from the three-dimensional image data; and displaying the generated slice image.

28. An image processing method used in an ultrasonic diagnostic apparatus comprising an ultrasonic probe and a scanning unit configured to scan a three-dimensional region in an object with an ultrasonic wave via the ultrasonic probe, the method comprising:

generating three-dimensional image data based on an output from the scanning unit;

specifying a slice from the three-dimensional image data, the specifying step including performing pattern matching between a sample image and MPR images obtained by rotating a slice angle around a calculated center axis to obtain a reference MPR image;

generating a slice image associated with the specified slice from the three-dimensional image data;

displaying the generated slice image;

executing a first phase in which the slice is specified from the three-dimensional image data; and executing a second phase in which the three-dimensional image data is repeatedly generated by repeating the three-dimensional scanning after the first phase, and a slice image associated with a slice specified in the first phase is generated and displayed from the three-dimensional image data.

29. An image processing method used in an ultrasonic diagnostic apparatus comprising an ultrasonic probe and a scanning unit configured to scan a three-dimensional region in an object with an ultrasonic wave via the ultrasonic probe, the method comprising:

generating three-dimensional image data based on an output from the scanning unit;

generating a slice image from the three-dimensional image data;

displaying the generated slice image;

executing a first phase in which a reference slice image is selected from a plurality of slice images generated from the three-dimensional image data; and executing a second phase in which the three-dimensional image data is repeatedly generated by repeating the three-dimensional scanning after the first phase, and a slice image exhibiting a highest correlation coefficient relative to the reference slice image selected in the first phase is selected and displayed using pattern matching from a plurality of slice images generated from the three-dimensional image data by rotating a slice angle around a calculated center axis.

30. The apparatus according to claim 1, wherein the image generating unit is configured to automatically detect an MPR image of a time phase or view set in a protocol for stress echo examination, the detected MPR image varying depending on the protocol.

31. The apparatus according to claim 1, wherein the slice specifying unit is configured to extract an MPR image by referring to an image pattern detected before application of a stress.

* * * * *